(12) United States Patent
Kingsman et al.

(10) Patent No.: US 6,541,219 B1
(45) Date of Patent: Apr. 1, 2003

(54) THERAPEUTIC GENE

(76) Inventors: Alan John Kingsman, Greystones, Middle Street, Islip, Oxon OX5 2SF (GB); Susan Mary Kingsman, Greystones, Middle Street, Islip, Oxon OX5 2SF (GB)

( * ) Notice: Subject to any disclaimer, the term of this patent is extended or adjusted under 35 U.S.C. 154(b) by 0 days.

(21) Appl. No.: 09/254,832

(22) PCT Filed: Oct. 28, 1997

(86) PCT No.: PCT/GB97/02969

§ 371 (c)(1), (2), (4) Date: Jun. 21, 1999

(87) PCT Pub. No.: WO98/18934

PCT Pub. Date: May 7, 1998

(30) Foreign Application Priority Data

Oct. 29, 1996 (GB) ............................................. 9622500

(51) Int. Cl.$^7$ ....................... C12N 15/867; C12N 15/63; C12N 5/10; C12P 21/02; A61K 48/00
(52) U.S. Cl. .................... 435/69.1; 435/320.1; 435/455; 435/456; 435/69.7; 435/325; 435/183; 536/23.1; 536/23.2; 536/23.4; 536/23.5; 536/24.1; 424/93.1; 424/93.2; 424/93.6
(58) Field of Search .............................. 424/93.1, 93.2, 424/93.6; 435/320.1, 455, 456, 69.1, 69.7, 325, 183; 536/23.1, 23.2, 23.4, 23.5, 24.1

(56) References Cited

U.S. PATENT DOCUMENTS

| | | | |
|---|---|---|---|
| 5,344,923 A | 9/1994 | Verma et al. | ............... 536/23.2 |
| 5,359,035 A | 10/1994 | Habermann | .................. 530/351 |

FOREIGN PATENT DOCUMENTS

| | | |
|---|---|---|
| WO | WO 89/12109 | 12/1989 |
| WO | WO 92/07945 | 5/1992 |
| WO | WO 94/12520 | 6/1994 |
| WO | WO 95/28493 | 10/1995 |
| WO | WO 95/34670 | 12/1995 |
| WO | WO 96/05319 | 2/1996 |
| WO | WO 96/37621 | 11/1996 |
| WO | WO 96/37623 | 11/1996 |
| WO | WO 97/18319 | 5/1997 |

OTHER PUBLICATIONS

E.B. Kmiec, American Scientist, vol. 87, pp. 240–247, Jun. 1999.*
Ross et al., Human Gene Therapy, vol. 7, pp. 1781–1790, Sep. 1996.*
Salmons et al., Human Gene Therapy, vol. 4, pp. 129–141, 1993.*
Verma et al., Nature, vol. 389, pp. 239–242, Sep. 1997.*
W. French Anderson, Nature, vol. 392, pp. 25–30, Apr. 1998.*
J. L. Fox, Nature Biotechnology, vol. 18, pp. 142–144, Jun. 1999.*

Marasco et al., "Design, intracellular expression, and activity of a human anti-human immunodeficiency virus type 1 gp120 single-chain antibody", Proc. Natl. Acad. Sci , vol. 90, 1993, Natl. Acad. Sci., Washington, D.C.
Nature Genetics, vol. 8, Oct. 1994, pp. 148–154, Kaplitt et al., "Long-term expression and phenotypic correction using adeno-associated virus vectors in the mammalian brain".
Science, vol. 266, Nov. 25, 1994, pp. 1399–1403, During et al., "Long-Term Behavioral Recovery in Parkinsonian Rats by an HSV Vector Expressing Tyrosine Hydroxylase".
neuroreport, vol. 6, No. 1, Dec. 30, 1994, Horellou et al., "Direct intracerebral gene transfer of an adenoviral vector expressing tyrosine hydroxylase in a rat model of Parkinson's disease".
Journal of Neurochemistry, vol. 56, No. 3, 1991, pp. 1030–1036, Owens et al., "L–3, 4–Dihydroxyphenylalanine Synthesis by Geneticall Modified Schwann Cells".
Science, vol. 272, Apr. 12, 1996, pp. 263–267, Naldini et al., "In Vivo Gene Delivery and Stable Transduction of Nondividing Cells by a Lentiviral Vector".
Journal of Virology , Jul. 1988, pp. 2464–2473, Bowtell et al., "Comparison of Expression in Hemopoietic Cells by Retroviral Vectors Carrying Two Genes".
Blood vol. 84, No. 6, Sep. 15, 1994, pp. 1812–1822, Correll et al., "Retroviral Vector Design for Long–Term Expression in Murine Hematopoietic Cells In Vivo".
Cell, vol. 39, Dec. 1984, pp. 459–467, Emermann et al., "Genes with Promoters in Retrovirus Vectors Can Be Independently Suppressed by an Epigenetic Mechanism".
Molecular and Cellular Biology, Dec. 1991, pp. 5848–5859, Ghattas et al., "The Encephalomyocarditis Virus Internal Ribosome Entry Site Allows Efficient Coexpression of Two Genes from a Recombinant Provirus in Cultered Cells and in Embryos".
Proc. Natl. Acad. Sci. USA, vol. 86, May 1989, pp. 3519–3523, Hantzopoulos et al., "Improved gene expressed upon transfer of the adenosine deaminase minigene outside the transcriptional unit of a retroviral vector".
The Journal of Biological Chemistry, vol. 266, No. 13, May 5, 1991, pp. 8416–8425, Hatzoglou et al., "Hormonal Control of Interacting Promoters Introduced into Cells by Retroviruses".
The Journal of Biological Chemistry, vol. 263, No. 33, Nov. 25, 1988, pp. 17798–17808, Hatzoglou et al., "Hormonal Regulation of Chimeric Genes Containing the Phosphoenolpyrusvate Carboxykinase Promoter Regulatory Region in Hepatoma Cells Infected by Murine Retroviruses".

(List continued on next page.)

Primary Examiner—David Guzo (57) ABSTRACT

Polynucleotide sequences and vectors containing them, for use in gene therapy, the polynucleotide sequences comprising two or more therapeutic genes operably linked to a promoter and encoding a fusion protein product of the therapeutic genes. The fusion protein may be for example a tyrosine hydroxylase (TH)-DOPA decarboxylase (DD) fusion in either TH-DD or DD-TH order, useful for treating Parkinson's disease.

11 Claims, 5 Drawing Sheets

OTHER PUBLICATIONS

Human Gene Therapy 3, 1992, pp. 381–390, Li et al, "Comparison of the Expression of a Mutant Dihydrofolate Reductase under Control of Different Internal Promoters in Retroviral Vectors".

Virology 195, 1993, pp. 1–5, McLachlin et al., "Factors Affecting Retroviral Vector Function and Structural Integrity".

Molecular and Cellular Biology, Apr. 1988, pp. 1803–1808, Overell et al., "Stably Transmitted Triple–Promoter Retroviral Vectors and Their Use in Transformation of Primary Mammalian Cells".

Proc. Natl. Acad. Sci. USA, vol. 88, Jun. 1991, pp. 4626–4630, Scharfmann et al., "Long–term in vivo expression of retrovirus–mediated gene transfer in mouse fibroblast implants".

Gene Therapy, 1994 1, pp. 307–316, Vile et al., "A comparison of the properties of different retroviral vectors containing the murine tyrosinase promoter to achieve transcriptionally targeted expression of the HSVtk or IL–2 genes".

Virology 171, 1989, pp. 331–341, Xu et al. "Factors Affecting Long–Term Stability of Moloney Murine Leukemia Virus–Based Vectors".

Proc. Natl. Acad. Sci. USA, vol. 84, Aug. 1987, pp. 5197–5201, Yee et al., "Gene expression from transcriptionally disabled retroviral vectors".

Journal of Virology, Sep. 1991, pp. 4985–4990, Adam et al., "Internal Initiation of Translation in Retroviral Vectors Carrying Piconavirus 5' Nontranslated Regions".

Proc. Natl. Acad. Sci. USA, Aug. 1993, vol. 90, pp. 7889–7893, Marasco et al., "Design, intracellular expression, and activity of a human anti–human immunodeficiency virus type 1 gp120, single–chain antibody".

Cell, vol. 54, Sep. 9, 1988, pp. 841–853, Wiederrecht et al., "Isolation of the Gene Encoding the *S. cerevisiae* Heat Shock Transcription Factor".

Nature, vol. 362, Apr. 29, 1993, pp. 852–855, Dekker et al., Solution structure of the POU–specific DNA–binding domain of Oct.–1.

Genes & Development 1, 1988, pp. 1582–1599, Sturm et al., "The ubiquitous octamer–binding protein Oct.–1 contains a POU domain with a homeo box subdomain".

FEBST Letters, vol. 262, No. 1, Mar. 1990, pp. 82–86, Aumailley et al., "Identification of the Arg–Gly–Asp sequence in laminin A chain as a latent cell–binding site being exposed in fragment P1".

Gene Therapy 1995, 2, pp. 750–756, Wickham et al, "Targeting of adenovirus penton base to new receptors through replacement of its RGD motif with other receptor–specific peptide motifs".

Proc. Natl. Acad. Sci. USA, vol. 83, May 1986, pp. 3194–3198, Yu et al., "Self–inactivating retroviral vectors designed for transfer of whole genes into mammalian cells".

Research Paper, Dec. 1995, pp. 315–324, Haas et al, "Codon usage limitation in the expression of HIV–1 envelope glycoprotein".

Letters to Nature, vol. 326, Apr. 1987, pp. 707–711, Grima et al., "A single human gene encoding multiple tyrosine hydroxylases with different predicted functional characteristics".

Biochemical And Biophysical Research Communications, vol. 146, No. 3, 1987, pp. 971–975, Kaneda et al, "Isolation of a novel cDNA clone for human tyrosine hydroxylase: Alternative RNA splicing produces four kind of mRNA from A single gene".

Proc. Natl. Acad. Sci. USA, vol. 92, Aug. 1995, pp. 7570–7574, Somia et al., "Generation of targeted retroviral vectors by using single–chain variable fragment: An approach to in vivo gene delivery".

Analytical Biochemistry 43, 1971, pp. 588–600, Waymire et al., "Assay of Tyrosine Hydroxylase by Coupled Decarboxylation of Dopa Formed from $1-^{14}C-L-$Tyrosine".

CSH Retrovirus Meeting abstract, 1996, Srinivasakumar et al., p. 318, "Requirement for Efficient Transfer of HIV–1 Vectors to target Cells using HIV–1 Based Packaging Cell".

Nature, vol. 293, Oct. 1981, pp. 543–548, Shinnick et al, "Nucleotide sequence of Moloney murine leukaemia virus".

Nucleic. Acids Research, 1995, vol. 23, No. 4, Soneoka et al, "A transient three–plasmid expression system for the production of high titer retroviral vectors".

Biotechniques 7, 1989, pp. 980–990, Miller et al., "Improved Retroviral Vectors for Gene Transfer and Expression".

Proc. Natl. Acad. Sci., USA, 1993, vol. 90, pp. 7889–7893, Marasco et al., "Design, intracellular expression, and activity of a human anti–human, immunodeficiency virus type 1 gp120 single–chain anti–body".

Analytical Biochemistry, 1984, vol. 139, pp. 73–76, Maria Anna Rosei et al., "Oxygraphic Assay of 3, 4–Dihydroxyphenylalanine Decarboxylase Activity by Coupled Reaction with Free and Immobilized Serum Amine Oxidase".

* cited by examiner

Fig.3.
PCR Primers

1) The thdd gene:

```
              HincII
TH5-1    CA CAG TCG ACC ATG CCC ACC CCC GAC GCC ACC A
                                              [SEQ ID NO:13]
              HindIII
TH3-1    CG TAC AAG CTT CGA TCC tcc acc tcc cga GCC ACC
         TCC GCC TGA ACC GCC TCC ACC GCC AAT GGC ACT CAG
         CGC ATG                               [SEQ ID NO:14]
              HindIII
DD5-1    AC GCA AAG CTT ATG AAC GCA AGT GAA TTC CGA
                                              [SEQ ID NO:15]
              SpeI
DD3-1    C TGG ACT AGT CTA CTC CCT CTC TGC TCG CAG CAC
                                              [SEQ ID NO:16]
```

2) The ddth gene:

```
              HincII
DD5-2    CA CAG TCG ACC ATG AAC GCA AGT GAA TTC CGA
                                              [SEQ ID NO:17]
              HindIII
DD3-2    CG TAC AAG CTT CGA TCC tcc acc tcc cga GCC
         ACC TCC GCC TGA ACC GCC TCC ACC CTC CCT CTC
         TGC TCG CAG CAC                      [SEQ ID NO:18]
              HindIII
TH5-2    AC GCA AAG CTT ATG CCC ACC CCC GAC GCC ACC A
                                              [SEQ ID NO:19]
              SpeI
TH3-2    C TGG ACT AGT CTA GCC AAT GGC ACT CAG CGC ATG
                                              [SEQ ID NO:20]
```

Fig. 4.

a) Lentivirus genome b) LLD vector

■ = LENTIVIRAL SEQUENCES

□ = HETEROLOGOUS SEQUENCES

Fig. 5.

a) Producer DNA b) Integrated LLD vector

THERAPEUTIC GENE

This invention relates to polynucleotide sequences encoding fusion proteins, for use in gene therapy in particular for Parkinson's disease. The invention also relates to vectors carrying the polynucleotide sequences, in particular retroviral vectors, and to their use in gene therapy.

Parkinson's disease (PD) is a common neurodegenerative disorder that afflicts the growing population of elderly people. Patients display tremor, cogwheel rigidity and impairment of movement. It is generally thought to be an acquired rather than inherited disease in which environmental toxins, metabolic disorders, infectious agents and normal ageing have all been implicated. PD is associated with the degeneration of nigrostriatal neurons which have their soma located in the substantia nigra. They send axonal projections to the basal ganglia and they use dopamine as their neurotransmitter. Some features of the disease can be controlled by the administration of L-DOPA, the metabolic precursor to dopamine, which diffuses across the blood brain barrier more effectively than dopamine itself. Unfortunately as the disease progresses the side effects of this treatment become unacceptable.

PD is an ideal candidate for gene therapy for several reasons. The clinical efficacy of systemic administration of L-DOPA suggests that restoration of neuronal circuitry is not essential for disease management. Therefore genetic manipulation of brain cells to provide local production of L-DOPA from tyrosine may be a realistic strategy for treatment. The biosynthesis of L-DOPA from tyrosine involves a single step suggesting that provision of tyrosine hydroxylase (TH) by genetic means may be sufficient and some success has been achieved using this strategy in small animals and in cell culture (Kaplitt et al., 1994 Nature Genetics 8, 148; During et al., 1994 Science 266, 1399; Horellou et al., 1994 Neuroreport 6, 49; Owens et al., 1991 J. Neurochem. 56, 1030). However, if one is to use local endogenous brain cells as L-DOPA factories for the treatment of PD in man it is likely that high levels of L-DOPA will be required to effect a treatment. These high levels must be efficiently converted to dopamine as the necessary neurotransmitter and primary therapeutic agent. It is likely therefore that it will be necessary not only to supply tyrosine hydroxylase but also DOPA decarboxylase (DD), the enzyme that converts L-DOPA to dopamine. This means that in a gene therapy strategy the genes for both of these enzymes will be required.

Amongst gene transfer systems retroviral vectors hold substantial promise for gene therapy. These systems can transfer genes efficiently and new vectors are emerging that are particularly useful for gene delivery to brain cells (Naldini et al., 1996 Science 272, 263). However, it is clear from the literature that retroviral vectors achieve the highest titres and most potent gene expression properties if they are kept genetically simple (PCT/GB96/01230; Bowtell et al., 1988 J.Virol. 62, 2464; Correll et al., 1994 Blood 84, 1812; Emerman and Temin 1984 Cell 39, 459; Ghattas et al., 1991 Mol.Cell.Biol. 11, 5848; Hantzopoulos et al., 1989 PNAS 86, 3519; Hatzoglou et al., 1991 J.Biol.Chem 266, 8416; Hatzoglou et al., 1988 J.Biol.Chem 263,17798; Li et al., 1992 Hum.Gen.Ther. 3, 381; McLachlin et al., 1993 Virol. 195, 1; Overell et al., 1988 Mol.Cell Biol. 8, 1803; Scharfman et al., 1991 PNAS 88, 4626; Vile et al., 1994 Gene Ther 1, 307; Xu et al., 1989 Virol. 171, 331; Yee et al., 1987 PNAS 84, 5197). This means only using a single transcription unit within the vector genome and orchestrating appropriate gene expression from sequences within the 5' LTR. If there is a need to express two enzymes, such as TH and DD, from a single retroviral vector the only solution would be to use an internal ribosome entry site (IRES) to initiate translation of the second coding sequence in a polycistronic message (Adam et al 1991 J.Virol. 65, 4985). However, the efficiency of an IRES is often low and tissue dependent making this strategy undesirable when one is seeking to maximise the efficiency of metabolic conversion of tyrosine through to dopamine. The present invention addresses these problems.

The present invention provides in one aspect a polynucleotide sequence for use in gene therapy, which polynucleotide sequence comprises two or more therapeutic genes operably linked to a promoter, and encodes a fusion protein product of the therapeutic genes. The invention thus provides a way of expressing two therapeutic genes from a single "chimeric gene".

In another aspect, the invention provides a vector carrying the polynucleotide sequence as described. The vector may be for example an expression vector such as a plasmid, or it may be a retroviral vector particle comprising an RNA genome containing the polynucleotide sequence as described herein.

In yet further aspects, the invention provides a DNA construct encoding the RNA genome for the retroviral vector particle; and a retroviral vector production system comprising a set of nucleic acid sequences encoding the components of the retroviral vector particle.

The invention further provides the use of retroviral vectors carrying the chimeric gene described herein, in gene therapy and in the preparation of a medicament for gene therapy; and a method of performing gene therapy on a target cell, which method comprises infecting and transducing the target cell using a retroviral vector particle as described herein. The invention further provides transduced target cells resulting from these methods and uses. The invention thus provides a gene delivery system for use in medicine.

In addition, the invention provides a polynucleotide sequence encoding a fusion protein comprising tyrosine hydroxylase and DOPA decarboxylase in either TH-DD or DD-TH order, linked by a flexible linker.

The therapeutic genes are chosen according to the effect sought to be achieved. The fusion protein has or is capable of having the desired activity of the therapeutic gene products. The product encoded by one or more of the therapeutic genes may be an enzyme. The fusion protein may thus display the activity of one or more enzymes. Where the therapeutic genes encode two different enzymes, the resulting fusion protein is a bifunctional enzyme. In the specific example described herein, the fusion protein comprises the enzymes tyrosine hydroxylase and DOPA dehydroxylase having enzyme activities as described above.

Preferably the therapeutic genes are linked by a sequence encoding a flexible linker. A suitable linker may comprise amino acid repeats such as glycine-serine repeats. The purpose of the linker is to allow the correct formation and/or functioning of the therapeutic gene products. It must be sufficiently flexible and sufficiently long to achieve that purpose. Where the therapeutic genes encode two different enzymes, the linker needs to be chosen to allow the functioning of both of the enzymes. The coding sequence of the flexible linker may be chosen such that it encourages translational pausing and therefore independent folding of the protein products of the therapeutic genes.

A person skilled in the art will be able to design suitable linkers in accordance with the invention. Some specific examples of suitable linkers are given below; it will be evident that the invention is not limited to these particular linkers.

1. (Gly-Gly-Gly-Gly-Ser)$_3$ (SEQ ID NO: 21) as described in Somia et al., 1993 PNAS 90, 7889.
2. (Gly-Gly-Gly-Gly-Ser)$_5$ (SEQ ID NO: 22), a novel linker.
3. (Asn-Phe-Ile-Arg-Gly-Arg-Glu-Asp-Leu-Leu-Glu-Lys-Ile-Ile-Arg-Gln-Lys-Gly-Ser-Ser-Asn) (SEQ ID NO: 23) from HSF-1 of yeast, see Wiederrecht et al., 1988 Cell 54, 841.
4. (Asn-Leu-Ser-Ser-Asp-Ser-Ser-Leu-Ser-Ser-Pro-Ser-Ala-Leu-Asn-Ser-Pro-Gly-Ile-Glu-Gly-Leu-Ser) (SEQ ID NO: 24) from POU-specific OCT-1, see Dekker et al., 1993 Nature 362, 852 and Sturm et al., 1988 Genes and Dev. 2, 1582.
5. (Gln-Gly-Ala-Thr-Phe-Ala-Leu-Arg-Gly-Asp-Asn-Pro-Gln-Gly) (SEQ ID NO: 25) from RGD-containing Laminin peptide, see Aumailly et al., 1990 FEBS Lett. 262, 82.
6. (Ser-Gly-Gly-Gly-Glu-Ile-Leu-Asp-Val-Pro-Ser-Thr-Gly-Gly-Ser-Ser-Pro-Gly) (SEQ ID NO: 26) from LDV-containing linker, see Wickham et al., Gene Therapy 1995 2, 750.

It will be evident that the term "gene" is used loosely here, and includes any nucleic acid coding for the desired polypeptide.

Vectors carrying the polynucleotide sequence encoding the fusion protein include any vectors suitable for use in gene therapy, that is, vectors which are capable of delivering the polynucleotide sequence encoding the fusion protein to a target cell. Particularly preferred vectors for use in the present invention are retroviral vectors, which have a number of well-documented advantages as vectors for gene therapy. The invention provides retroviral vectors with further advantages for gene therapy, because it enables the construction of a simplified retroviral vector for delivering therapeutic genes. In particular it enables the construction of retroviral vectors capable of delivering multiple therapeutic genes in a single transcription unit. Multiple therapeutic genes in a single transcription unit are operably linked to the same promoter and are all transcribed under the control of that promoter. There is no more than one promoter active in respect of the single transcription unit at any one time.

Preferably, the retroviral vector according to the invention is a single transcription unit vector, that is, the vector genome in DNA or RNA form is under the transcriptional control of no more than one vector promoter at any one time. In a preferred embodiment, this is achieved by locating the polynucleotide sequence according to the invention such that in the DNA form of the vector genome integrated into the target cell genome (the DNA provirus), it is under transcriptional control of the 5' LTR. There are alternative ways of achieving a single transcription unit vector, however. The vector genome could be designed as a self-inactivating vector (Yu et al., 1986 PNAS 83, 3194) in which part of the 3' U3 sequences are deleted so that the transduced vector genome has a non-functional 5' LTR promoter. The polynucleotide sequence according to the invention would be operably linked to an internal conditional promoter between the LTRs which could be activated once the vector has transduced a target cell. Activation of the promoter might be dependent upon cellular or external factors.

Although single transcription unit vectors are preferred, other vectors are not excluded. It may be useful for example to include a marker gene in the vector, operably linked to a different promoter which may be active simultaneously with the promoter responsible for transcription of the polynucleotide sequence encoding the fusion protein. A marker gene encoding a selectable marker may be useful for selecting successfully transfected packaging cells, or successfully transduced target cells. Marker genes encoding selectable markers may be for instance drug resistance genes or metabolic enzyme genes.

The retroviral vector according to the invention may be constructed according to methods known in the art. Retroviral vectors suitable for gene therapy will need to be replication defective. Particular factors to be taken into consideration when constructing a retroviral vector include safety aspects and the avoidance of undesirable immune responses. Preferably, the retroviral vector genome which will be inserted into the target cell in the form of a DNA provirus contains the minimum retroviral material necessary to function. This avoids both the possible reconstruction of infectious virus particles, and expression of unwanted virus proteins in the target cell which could otherwise evoke undesirable immune responses in the patient being treated.

For the production of retroviral vector particles, the vector RNA genome is expressed from a DNA construct encoding it, in a host cell. The components of the particles not encoded by the vector genome are provided in trans by additional nucleic acid sequences (the "packaging system", which usually includes either or both of the gag,pol and env genes) expressed in the host cell. The set of sequences required for the production of the retroviral vector particles may be introduced into the host cell by transient transfection, or they may be integrated into the host cell genome, or they may be provided in a mixture of ways. The techniques involved are known to those skilled in the art.

To date, the most widely used retroviral vector systems for human gene therapy applications have used MLV. However, retroviral vector systems may also be based on other oncoretroviruses (the sub-group of retroviruses containing MLV), or lentiviruses (the subgroup of retroviruses containing HIV, SIV, FIV, BLV, EIAV, CEV and visna virus), or retroviruses from other subgroups. A range of retroviruses have already been split into packaging and vector components for retroviral vector particle production systems, including ASLV, SNV and RSV. It will be evident that a retroviral vector according to the invention need not be confined to the components of a particular retrovirus. The retroviral vector may comprise components derived from two or more different retroviruses, and may also comprise synthetic components. Vector components can be manipulated to obtain desired characteristics, such as target cell specificity.

Certain retroviruses have special characteristics which may be useful in particular gene therapy applications. For example, the lentiviruses such as HIV are capable of infecting and transducing non-dividing cells because they have means for getting the proviral DNA across the nuclear membrane of target cells. This feature will be useful if it is desired to target non- or slowly-dividing cell types in gene therapy. Such cell types include the neurons of the human brain, which are a potentially important target for gene therapy treatment of Parkinson's disease. A retroviral vector particle according to the invention may thus be derived from a lentivirus, at least to the extent that it is capable of delivering proviral DNA efficiently to a non-dividing or slowly-dividing cell.

In the particular embodiment described herein, the invention addresses the problems of the prior art by providing a single fusion gene that expresses a fusion protein composed of TH and DD. The single gene encodes a single protein with both enzyme activities. This permits the construction of a simple single transcription unit retroviral vector that expresses both enzyme activities efficiently. The fusion gene is designed such that the enzymes are linked via a flexible linker, the coding sequence of which has a short cluster of infrequently used codons (Haas et al., 1996 Curr. Biol. 6, 315) to encourage translational pausing and, therefore, independent folding of the two domains of the new bifunctional enzyme. Two different types of fusion gene were made. In the first the order of the enzyme activities is TH-DD and in the other it is DD-TH. Both types are made because they may have different advantages and properties under different conditions. Human tyrosine hydroxylase is encoded by a single gene which is alternatively spliced to create four types of TH that differ towards their amino terminus (Grima et al., 1987 Nature 326, 707; Kaneda et al., 1987 BBRC 146, 971). However, identical primers can be used to isolate all four cDNAs by PCR as the termini are the same.

The invention will now be further described in the Examples which follow.

EXAMPLES

Example 1

Figure 1:
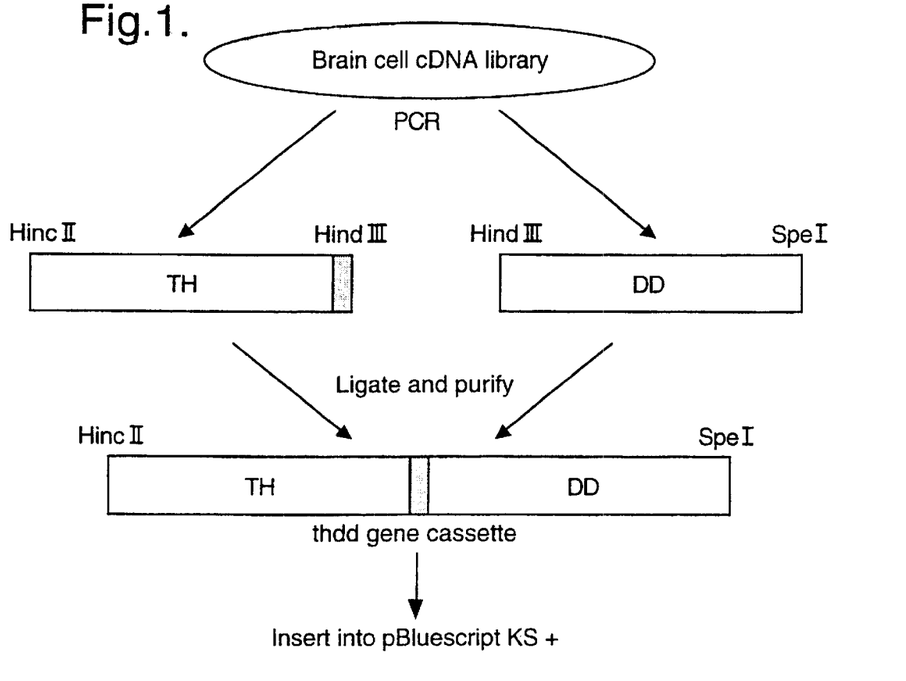
FIGS. 1 and 2 show simplified directions for construction of polynucleotide sequences according to the invention, encoding TH-DD and DD-TH fusion proteins.

Construction of TH-DD Fusion Genes Designated thdd1–4 (FIG. 1)

Figure 3:
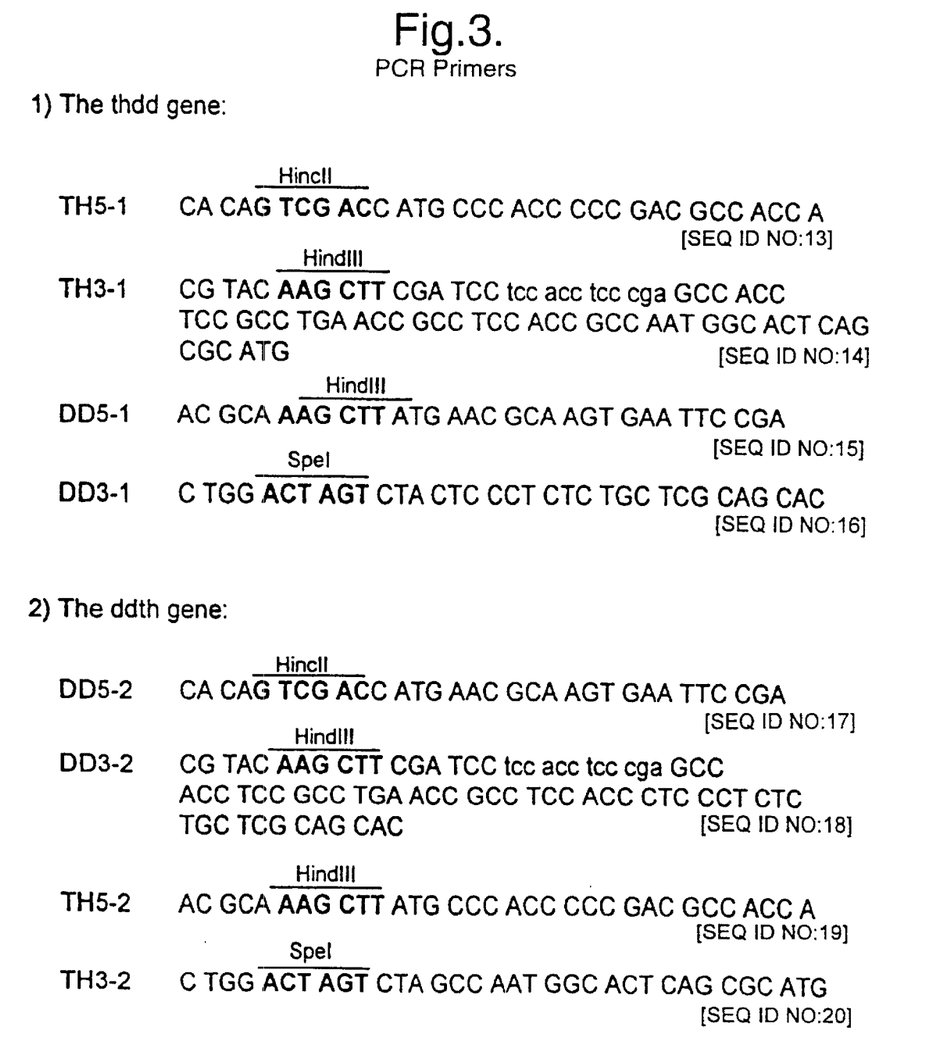
FIG. 3 shows primers for use in the construction methods illustrated in FIGS. 1 and 2 and described in detail in the Examples.
Figure 4:
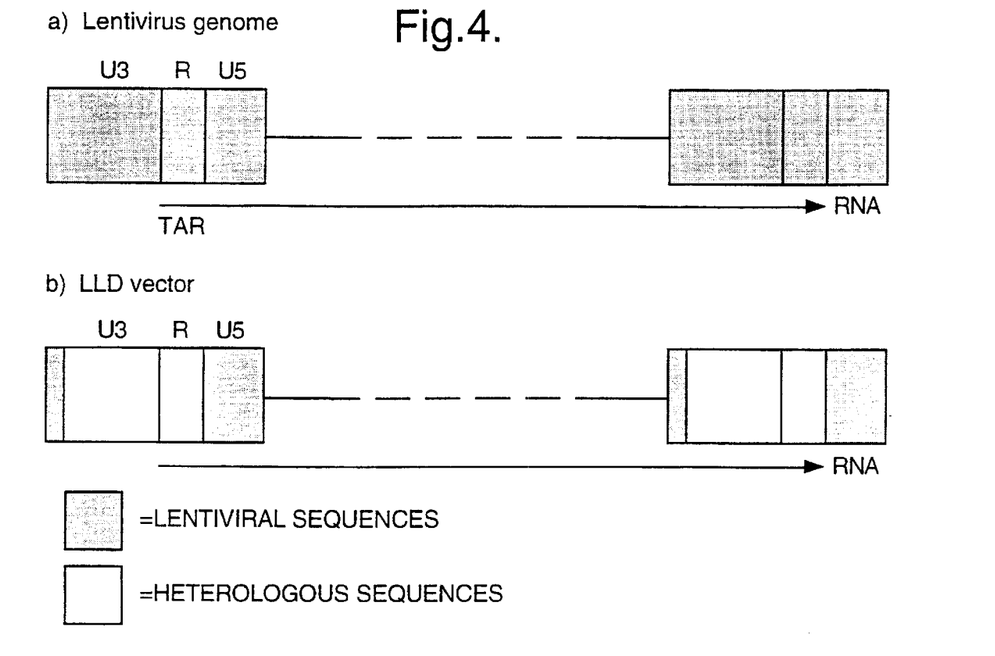
FIG. 4 shows a general scheme for Lentiviral LTR-deleted (LLD) vectors which may be used with the present invention and which are employed in the Examples.

A human brain *Substantia nigra* cDNA library (Clontech. HL3009a & b) is used as template DNA in a PCR amplification of the TH and DD cDNAs. The primers are shown in FIG. 3. In the case of the four TH cDNAs representing the HTH-1 to HTH-4 genes (Grima et al; Kaneda et al), they are all treated in the same way from a pool of PCR products and then identified after cloning and sequencing. The TH PCR products are produced from linkers containing a HincII site at the 5' end of the gene and a flexible linker and HindIII site at the 3' end. The flexible linker amino acid sequence is $(Gly_4-Ser)_3$ (SEQ ID NO: 21), a sequence often used to link the two chains of an antibody to produce an scFv (e.g. Somia et al., 1995 PNAS 92, 7570). The human DD PCR product was designed to have a HindIII site at the 5' end and a SpeI site at the 3' end. The two fragment are ligated and the ligated products of the correct size (2.98 kb, 2.99 kb, 3.06 kb and 3.07 kb for the four variants) are purified from an agarose gel. The purified fragments are then inserted into pBLUEscriptKS+ using HincII and SpeI. This ligation mixture is used to transform *E.coli* (XL2-Blue ex. Stratagene 200249) and clones were used to prepare DNA which is then sequenced to ensure that the genes are intact and to identify HTH1–4. Plasmids containing fragments encoding the four different HTH coding sequences fused to DD are designated pthdd1–4. The HincII-SpeI fragments from these plasmids are then inserted into the mammalian expression vector pCI-neo (Promega E1841). This is achieved by cutting pCI-neo with XhoI and SmaI and cutting the pBluescriptKS+ derived plasmids with SpeI and blunt ending and then cutting with XhoI. The cut products are then ligated together and correct plasmids checked by minipreps. The pCI-neo plasmids containing the fusion genes are designated pCIthdd1–4. These are then used to transiently transfect 293T cells which are then assayed for TH and DD by the methods of Waymire et al. (1971) (Anal.Biochem. 43, 588) and the method described in Anal. Biochem. (1984 139, 73). In each case significantly increased levels of TH and DD are seen compared with control cells transfected only with pCI-neo. This demonstrates that the fusion genes expresses fusion proteins with both activities.

Example 2

Figure 2:
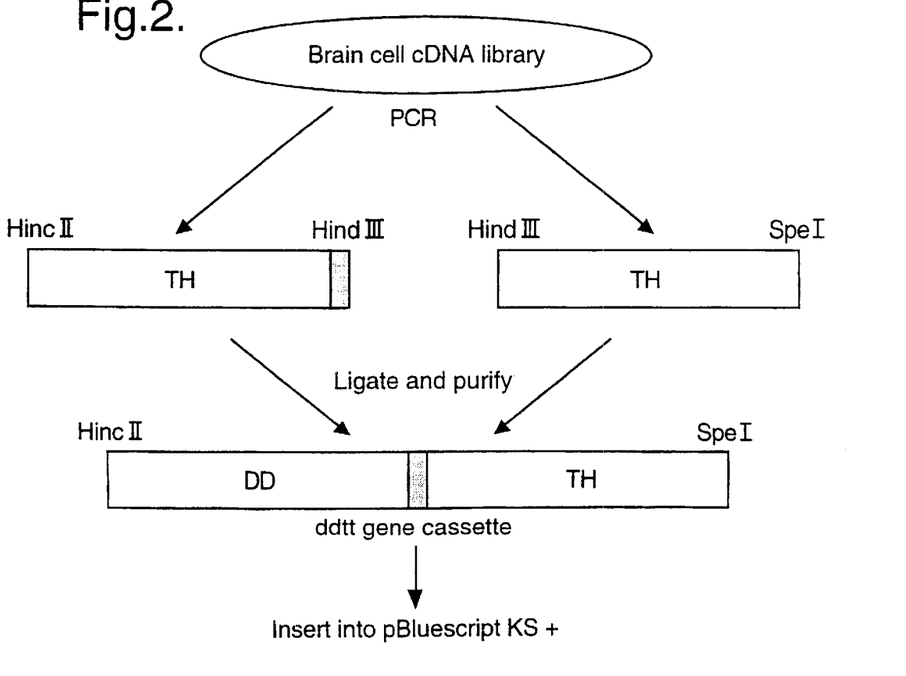

Construction of DD-TH fusion genes designated ddth1–4 (FIG. 2)

The construction of these genes is identical to that of Example 1 but the DD and TH coding sequences are in reciprocal locations. Similarly dual enzyme activities are encoded by the ddth1–4 genes.

Example 3

Construction of a Retroviral Vector Expressing a thdd Gene is a Single Transcription Unit Configuration The thdd and ddth genes are useful for the gene therapy of Parkinson's disease. They can be used in a wide range of vectors but they are particularly suited to single transcription unit retroviral vectors. An example of such a vector is produced as follows: Starting with pLNSX (Miller) a polylinker is inserted into the vector. Briefly, a SspI/HindIII fragment, containing the polylinker from pBluescriptKS+ is inserted into pLNSX cut with Ssp1 and HindIII. The resulting plasmid is known as pMLD1. Plasmid, pX1, for example, is then cut with SpeI and then the ends filled in with DNA polymerase. The plasmid is then cut again with XhoI. The resulting thdd fragment is then inserted into pMLD1 cut with XhoI and ClaI (blunt-ended) to produce the resulting molecule pMLD1:thdd1. When this plasmid is used to transfect a packaging cell line retroviral vectors are produced which transduce susceptible cells with the thdd gene in a single transcription unit configuration. In this case the gene is expressed from the MLV LTR promoter but any promoter inserted into the 5' LTR via a U3 replacement or similar strategy would be equally effective.

Example 4

Construction of a Lentiviral Vector Expressing a thdd Gene in a Single Transcription Unit Configuration Lentiviral vectors are particularly useful for gene transfer to non-dividing cells. Amongst many important non-dividing target cells are the neurons of the human brain. These cells might be target cells for the delivery of thdd or ddth cells for the treatment of Parkinson's disease. Here we describe the construction of an HIV based vector which will deliver and express thdd or ddth genes.

The vector that is used here is referred to as LLD1 (Lentiviral LTR-Deleted 1).

Figure 5:
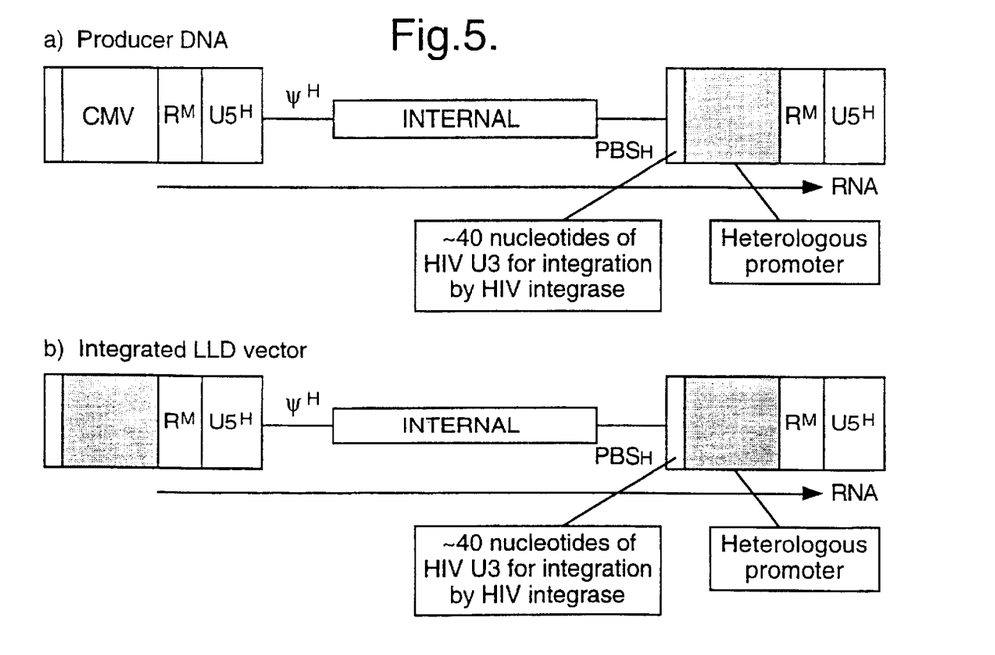
FIGS. 5 and 6 show a generalised and a specific HIV-based LLD vector genome as described in the Examples.
Figure 6:
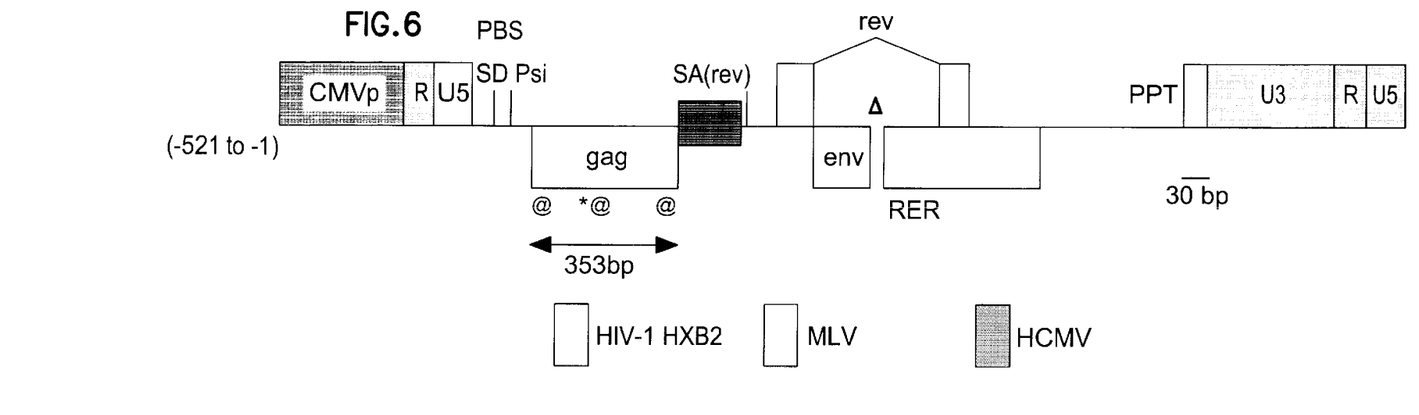
Figure 7:
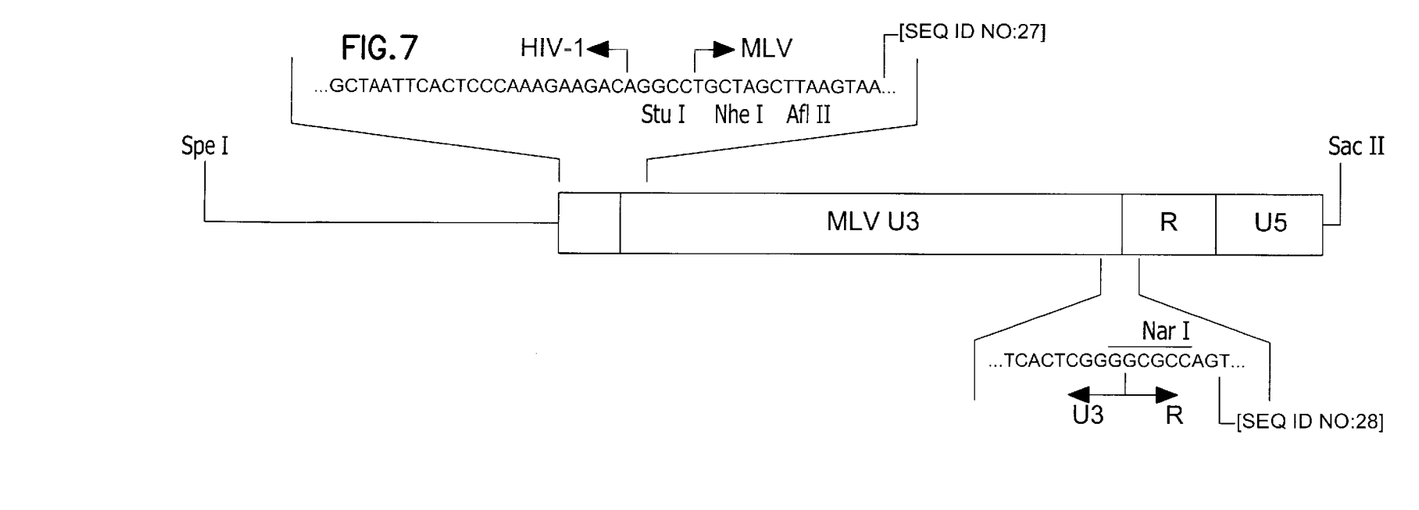
FIG. 7 shows in detail the structure of the 3' LTR for the vector in FIG. 6.

The structure of a general HIV LLD vector system is shown in FIG. 5. LLD1 is shown in FIGS. 6 and 7. It is constructed as follows. The minimal requirements for HIV reverse transcription are the primer binding site (PBS) to initiate the negative strand DNA synthesis, the polypurine tract (PPT) to initiate the positive DNA synthesis, and identical 5' and 3' R sequences to allow the first template switch. The incorporation of the PBS and PPT from HIV-1 into the vector and the R sequences from MLV into both LTRs is therefore required. As secondary structure within the 5' U5 region might be important for reverse transcription, the U5 region in the 5' LTR is from HIV-1. For the U5 region at the 3' LTR, the U5 from HIV-1 was used to make sure correct termination of transcription occurred at the R-U5 border. However, any termination signals could be used. For efficient integration, 30 nucleotides at the 5' end of the HIV-1 U3 at the 3' LTR were incorporated.

In order for the MLV U3 element to appear in the 5' LTR after reverse transcription, it must be in the 3' LTR of the viral RNA. The whole MLV U3 except 30 bps of the 5' end replaced the HIV-1 U3. The 3' LTR of the vector was designed to contain several convenient restriction sites, so that the MLV U3 can be easily replaced by other heterologous promoters (FIG. 7). Any heterologous promoters will be amplified by PCR with primers containing StuI and NarI sites at each end and will be used to replace the MLV U3. Not only StuI but also NheI and AflIII may be used at the 5' end of the promoter cassettes. NarI(GGCGCC) is located on the junction between the promoer and R, so that the transcription start site from he heterologous promoter can be preserved. The MLV U3 sequences between XbaI and NarI contains the basic promoter elements including TATA box, GC box, and CAAT box. Therefore the MLV enhancer can be replaced by any other enhancers as a StuI (or NheI or AflIII)—XbaI cassettes.

For efficient packaging 353 nucleotides of gag is known to be sufficient (Srinivasakumar et al., 1996 CSH Retrovirus Meeting abstract). The 353 nucleotides of gag sequences corresponds to the sequences from 790 to 1144, within this three ATG's (790, 834, 894) were removed by mutation. In addition a polycloning site is located downstream of gag.

In order to achieve efficient export of RNA species encoded by HIV genome, rev and RRE are required. They are included in the LLD vector and correspond to sequences 5861 to 6403 and 7621 to 9085 from HIV-1 (HXB2). Tat coding sequence is not present in the vector.

Details of Construction of the Producer DNA

A. 5' Structure (All HIV-1 coordinates are from HXB from the Los Alamos Sequence Database and MoMLV sequences are from Shinnick et al 1981 Nature 293. 543)

The 5' half of the vector contains the hybrid 5' LTR (CMV promoter-MLV R -HIV-1 U5), HIV-1 PBS, and HIV-1 packaging signal. This will be constructed by recombination PCR. One of the templates for the PCR, pHIVdge2, is an HIV-1 proviral DNA which has a mutation created by filling-in and religation at the ClaI site (831) and a deletion between NdeI(6403) and BglII(7621). The junction between MLV R and HIV-1 U5 is created by two primary PCR reactions (using the primer NIT1 and NIT2; NIT3 and NIT4) and a secondary PCR reaction (using the primers NIT1 and NIT4). The PCR product is inserted into pBluesriptKS+ (STRATAGEN) at KpnI and XhoI site (Construct A1). In order to mutate three ATGs in the gag region, the primers contain mutated codons.

NIT1: 5'-ccgggtacccgtattcccaataaagcctcttgctgtttgca-3' (SEQ ID NO: 1)

NIT2: 5'-ctacgatctaattctcccccgcttaatactgacgctctcgcacctatctc-3' (SEQ ID NO: 2)

NIT3: 5'-gcggggagaattagatcgtagggaaaaaattcggttaaggccagg gggaaagaaaaaatataaattaaaacatatagtttggg-3' (SEQ ID NO: 3)

NIT4: 5'-gaattctcgaggcgtgctgtgcttttttctatc-3' (SEQ ID NO: 4)

The CMV promoter—MLV R fragment is amplified by PCR from pRV109 (Soneoka et al., 1995 Nucl. Acids Res. 23, 628) to contain KpnI sites at both ends using the PCR primers NIT5 and NIT6 and inserted into construct A1 to produce construct A2.

NIT5: 5'-taggtacccgttacataacttacggtaaatg-3' (SEQ ID NO: 5)

NIT6: 5'-agaggctttattgggaatacg-3' (SEQ ID NO: 6)

B. 3' Structure

The 3' half of the vector genome includes the HIV-1 rev coding region and RRE, PPT, 36 bp of 5' end of HIV-1 U3, and the whole MLV LTR except 30 bp of 5'end. The sequences (5861–6000) are PCR amplified from pHIVdge2 (using NIT7 and NIT8) and are subcloned into pSP64 (PROMEGA) at BamHI and SacI site (Construct B1).

NIT7: 5'-cacggatccactagttggaagcatccaggaagtcagc-3' (SEQ ID NO: 7)

NIT8: 5'-ctctgactgttctgatgagc-3' (SEQ ID NO: 8)

The SacI-SacI fragment (6000–6403 and 7621–9572) from pHIVdge2 is inserted into the above construct to produce construct B2. Finally the HIV-1-MLV hybrid LTR will be created by two primary PCRs (using NIT9 and NIT10 with pHIVdge2 as the template; NIT11 and NIT12 with pLXSN (Accession number M28248; Miller et al., 1989) as the template) and one secondary PCR reaction (using NIT9 and NIT12). The PCR product will be inserted at the XhoI and EcoRI sites in Construct B2 to produce Construct B3.

NIT9: 5'-agcagcatctcgagacctgg-3' (SEQ ID NO: 9)

NIT10: 5'-tggcgttacttaagctagcaggcctgtctctttgggagtgttttagc-3' (SEQ ID NO: 10)

NIT11: 5'-cccaaagaagacaggcctgctagcttaagtaacgccattttcc-3' (SEQ ID NO: 1)

NIT12: 5'-ctgaattccgcggaatgaaagacccccgctgacg-3' (SEQ ID NO: 12)

C. Complete Vector

Figure 8:
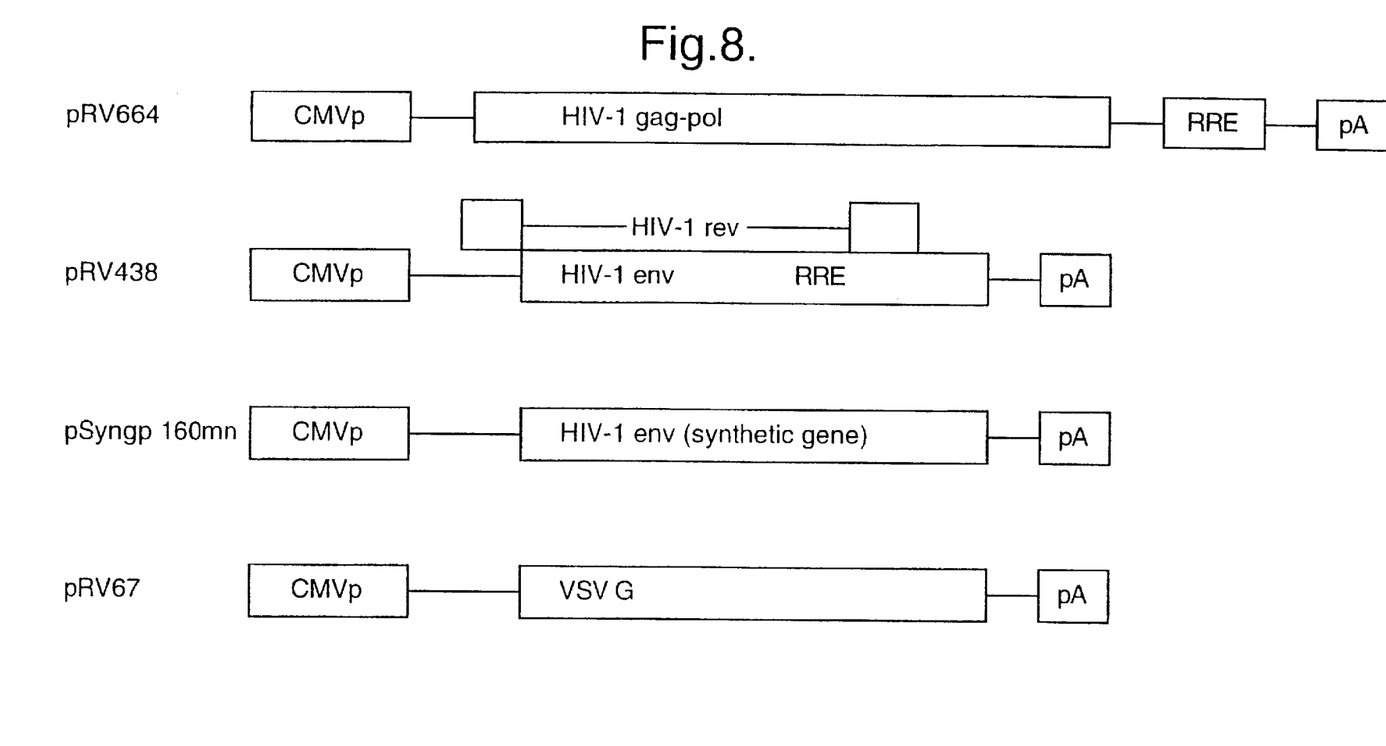
FIG. 8 is a schematic diagram of packaging components suitable for use with the vector genome shown in FIGS. 4 to 6.

The two halves of the vector are combined by inserting the SpeI-SacII fragment from construct B3 into construct A2. The resulting construct, C1, possesses a poly-cloning site; XhoI-SalI-ClaI-HindIII-EcoRV-EcoRI-PstI-SmaI-BamHI-SpeI (underlined sites are unique in the vector). This plasmid is designated pLLD1 and the retroviral vector that it produces is LLD1.

ddth1 is used to illustrate the principle but any of the fusion genes could be used. Plasmid pX1 is cut with HincII and SpeI and the fragment purified. This is then inserted into LLD1 cut with EcoRV and SpeI to create pLLD1:thdd1. When this is transfected into a packaging cell line (suitable packaging components are shown in FIG. 8) and viral vector particles produced, those vector particles deliver the thdd gene to the recipient cells where the fusion enzymes are expressed. Such a retroviral vector system is useful for the treatment of Parkinson's disease by gene therapy.

FIGURE LEGENDS

FIG. 3

Lower case nucleotides denote rare codons in highly expressed genes in mammalian cells (Haas et al., 1996 Cur. Biol. 6, 315).

FIG. 5

Superscript H=HIV-derived sequence (Could be from any lentivirus)

Superscript M=MLV-derived sequence

ψ=Packaging site (including gag region)

PBS=Second strand priming site

INTERNAL=Region containing genes, selectable markers, other promoters or RNA handling systems such as HIV RRE and Rev coding sequences.

FIG. 6

NIT vector genome (Inserts 3789 bp+backbone 2929 bp=6718 bp):

HCMV promoter (−521 to −1) from pRV109

HIV sequences (552 to 1144; 5861 to 6403; 7621 to 9085) from HXB2

Genotype: gag-;pol-;env-;rev+;RRE; vif-;vpu-;vpr-;tat-;nef-

Mutations; three point mutations to remove ATG (790, 834, 894) (@)

a frameshift mutation by two base insertion (831) (*)

a deletion between NdeI (6403) and BglII(7621) (Δ)

Polycloning site (X); XhoI-SalI-ClaI-EcoRV-EcoRI-PstI-SmaI-SmaI-BamHI-SpeI: Underlined sites are unique.

Maximal insertion size into the polycloning site: 5997 bp

Backbone: pBluescriptKS+

FIG. 8 pRV664 encodes HIV-1 HXB2 gagpol (637–5748) and contains RRE (7720–8054) and its backbone is pCI-neo (PROMEGA).

pRV438 possesses both rev and env from HXB2 (5955–8902) in pSA91 which is a mammalian expression plasmid with CMC promoter. pSyngp 160 mn (from B. Seed) is an expression plasmid for HIV-1 MN envelope which was modified to have the optimized codon usage in mammalian cells. pRV67 is a VSV G expression plasmid in pSA91.

---

What is claimed is:

1. A lentiviral-based vector capable of transducing a non-dividing cell, said vector comprising a sequence encoding a fusion protein, said sequence comprising two or more therapeutic genes operably linked to a promoter.

2. The vector according to claim 1, wherein the fusion protein is encoded by a sequence comprising tyrosine hydroxylase and a sequence encoding DOPA decarboxylase, wherein the sequences encoding tyrosine hydroxylase and DOPA decarboxylase are operably linked by a sequence encoding a flexible linker.

3. The vector according to claim 1, wherein the lentiviral-based vector comprises a lentviral LTR-deleted vector.

4. The polynucleotide sequence according to claim 1, wherein the flexible linker comprises glycine-serine amino acid repeats.

5. The vector according to claim 1, comprising a single transcription unit comprising the sequences encoding tyrosine hydroxylase and DOPA decarboxylase.

6. A method for producing a bifunctional fusion protein in a non-dividing cell, said method comprising:
providing a non-dividing cell;
transducing the non-dividing cell with the vector according to claim 1; and
expressing the bifunctional fusion protein in the cell, wherein the bifunctional fusion protein comprises tyrosine hydroxylase and DOPA decarboxylase.

7. A target cell in vitro, comprising the lentiviral vector of claim 1.

8. The vector according to claim 5, wherein the single transcription unit is under transcriptional control of the 5' LTR.

9. A lentiviral vector comprising a sequence encoding a fusion protein comprising tyrosine hydroxylase and DOPA decarboxylase, wherein tyrosine hydroxylase and DOPA decarboxylase are operably connected by a flexible linker.

10. A method for producing a bifunctional fusion protein comprising tyrosine hydroxylase and DOPA decarboxylase in a neuron, said method comprising:
providing a neuron;
transducing the neuron with the vector according to claim 9; and
expressing the bifunctional fusion protein in the neuron, wherein the bifunctional fusion protein possesses the activity of both tyrosine hydroxylase and DOPA decarboxylase.

11. The method according to claim 6, wherein the non-dividing cell is a neuron.

* * * * *

SEQUENCE LISTING

```
<160> NUMBER OF SEQ ID NOS: 28

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence:  Synthetic

<400> SEQUENCE: 1
ccgggtaccc gtattcccaa taaagcctct tgctgtttgc a                    41

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence:  Synthetic

<400> SEQUENCE: 2
ctacgatcta attctccccc gcttaatact gacgctctcg cacctatctc           50

<210> SEQ ID NO 3
<211> LENGTH: 84
<212> TYPE: DNA
<213> ORGANISM: Artificial Sequence
<220> FEATURE:
<223> OTHER INFORMATION: Description of Artificial Sequence:  Synthetic

<400> SEQUENCE: 3
gcgggggaga attagatcgt agggaaaaaa ttcggttaag gccaggggga aagaaaaat  60 ataaattaaa acatatagtt tggg                                       84

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence:  Synthetic
```

-continued

```
<400> SEQUENCE: 4
gaattctcga ggcgtgctgt gctttttttct atc                              33

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic

<400> SEQUENCE: 5
gtaggtaccc gttacataac ttacggtaaa tg                                32

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 6
agaggcttta ttgggaatac g                                            21

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 7
cacggatcca ctagttggaa gcatccagga agtcagc                           37

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 8
ctctgactgt tctgatgagc                                              20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 9
gagcagcatc tcgagacctg g                                            21

<210> SEQ ID NO 10
<211> LENGTH: 48
<212> TYPE: DNA
<213> ORGANISM: Artificial Sequence
<220> FEATURE:
<223> OTHER INFORMATION: Description of Artificial Sequence: Synthetic

<400> SEQUENCE: 10
tggcgttact taagctagca ggcctgtctt ctttgggagt gttttagc                48

<210> SEQ ID NO 11
<211> LENGTH: 44
```

```
<212> TYPE: DNA
<213> ORGANISM: Artificial Sequence
<220> FEATURE:
<223> OTHER INFORMATION: Description of Artificial Sequence: Synthetic

<400> SEQUENCE: 11
cccaaagaag acaggcctgc tagcttaagt aacgccattt ttcc                        44

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic

<400> SEQUENCE: 12
cctgaattcc gcggaatgaa agaccccgc tgacg                                   35

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic

<400> SEQUENCE: 13
cacagtcgac catgcccacc cccgacgcca cca                                    33

<210> SEQ ID NO 14
<211> LENGTH: 77
<212> TYPE: DNA
<213> ORGANISM: Artificial Sequence
<220> FEATURE:
<223> OTHER INFORMATION: Description of Artificial Sequence: Synthetic

<400> SEQUENCE: 14
cgtacaagct tcgatcctcc acctcccgag ccacctccgc ctgaaccgcc tccaccgcca       60
atggcactca gcgcatg                                                      77

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic

<400> SEQUENCE: 15
acgcaaagct tatgaacgca agtgaattcc ga                                     32

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 16
ctggactagt ctactccctc tctgctcgca gcac                                   34

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic
```

```
<400> SEQUENCE: 17
cacagtcgac catgaacgca agtgaattcc ga                                  32

<210> SEQ ID NO 18
<211> LENGTH: 77
<212> TYPE: DNA
<213> ORGANISM: Artificial Sequence
<220> FEATURE:
<223> OTHER INFORMATION: Description of Artificial Sequence: Synthetic

<400> SEQUENCE: 18
cgtacaagct tcgatcctcc acctcccgag ccacctccgc ctgaaccgcc tccaccctcc    60
ctctctgctc gcagcac                                                   77

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic

<400> SEQUENCE: 19
acgcaaagct tatgcccacc cccgacgcca cca                                 33

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 20
ctggactagt ctagccaatg gcactcagcg catg                                34

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 21

Gly Gly Gly Gly Ser Gly Gly Gly Gly Ser Gly Gly Gly Gly Ser
 1               5                  10                  15

<210> SEQ ID NO 22
<211> LENGTH: 25
<212> TYPE: PRT
<213> ORGANISM: Artificial Sequence
<220> FEATURE:
<223> OTHER INFORMATION: Description of Artificial Sequence: Synthetic

<400> SEQUENCE: 22

Gly Gly Gly Gly Ser Gly Gly Gly Gly Ser Gly Gly Gly Gly Ser Gly
 1               5                  10                  15

Gly Gly Gly Ser Gly Gly Gly Gly Ser
            20                  25

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence: Synthetic
```

-continued

```
<400> SEQUENCE: 23

Asn Phe Ile Arg Gly Arg Glu Asp Leu Leu Glu Lys Ile Ile Arg Gln
1               5                   10                  15

Lys Gly Ser Ser Asn
            20

<210> SEQ ID NO 24
<211> LENGTH: 23
<212> TYPE: PRT
<213> ORGANISM: Artificial Sequence
<220> FEATURE:
<223> OTHER INFORMATION: Description of Artificial Sequence: Synthetic

<400> SEQUENCE: 24

Asn Leu Ser Ser Asp Ser Ser Leu Ser Ser Pro Ser Ala Leu Asn Ser
1               5                   10                  15

Pro Gly Ile Glu Gly Leu Ser
            20

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 25

Gln Gly Ala Thr Phe Ala Leu Arg Gly Asp Asn Pro Gln Gly
1               5                   10

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic

<400> SEQUENCE: 26

Ser Gly Gly Gly Glu Ile Leu Asp Val Pro Ser Thr Gly Gly Ser Ser
1               5                   10                  15

Pro Gly

<210> SEQ ID NO 27
<211> LENGTH: 43
<212> TYPE: DNA
<213> ORGANISM: Artificial Sequence
<220> FEATURE:
<223> OTHER INFORMATION: Description of Artificial Sequence: Synthetic

<400> SEQUENCE: 27
gctaattcac tcccaaagaa gacaggcctg ctagcttaag taa                     43

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence: Synthetic

<400> SEQUENCE: 28
tcactcgggg cgccagt                                                  17
```